United States Patent [19]
Beck

[11] Patent Number: 5,710,326
[45] Date of Patent: Jan. 20, 1998

[54] CATALYST REGENERATION PROCESS

[75] Inventor: Carl R. Beck, Baton Rouge, La.

[73] Assignee: Exxon Chemical Patents Inc., Linden, N.J.

[21] Appl. No.: 695,165

[22] Filed: May 3, 1991

[51] Int. Cl.$^6$ .................................................. C07C 51/14
[52] U.S. Cl. ................................................... 562/521
[58] Field of Search ..................................... 562/521

[56] References Cited

U.S. PATENT DOCUMENTS

| | | | |
|---|---|---|---|
| 3,349,107 | 10/1967 | Pawlenko | 260/410.9 |
| 3,527,779 | 9/1970 | Paulis et al. | 260/413 |
| 4,518,798 | 5/1985 | Kramer et al. | 560/233 |

FOREIGN PATENT DOCUMENTS 1252675  12/1960  France .

OTHER PUBLICATIONS

USSR reference SU1487922, Jun. 23, 1989, Babaev, A.I.; Ismailov, T.I.; Levin, V.L.

W. J. Ellis and C. Roming, Jr., Hydrocarbon Processing, "Make Low–Cost Carboxylic Acids From Olefins, Carbon Monoxide and Water", Jun. 1965, vol. 44, No. 6, pp. 139–141.

*Primary Examiner*—Marianne M. Cintins
*Assistant Examiner*—Keith MacMillan

[57] ABSTRACT

A process for controlling the regeneration of boron trifluoride catalyst complexes in the production of carboxylic acids and other products using boron trifluoride hydrates as a catalyst. Catalyst strength is determined by measuring the electrical conductivity of the catalyst recovered from hydrolysis. If the conductivity is greater than a predetermined value, the hydrolysis water rate is reduced and if the conductivity is leas than a predetermined value, the hydrolysis water rate is increased. Conductivity is determined by a toroidal conductivity sensor and a control valve responsive to operation of the conductivity sensor serves to increase or decrease the flow rate accordingly.

6 Claims, 4 Drawing Sheets

NEO ACIDS PROCESS

SP = CATALYST SAMPLE POINT

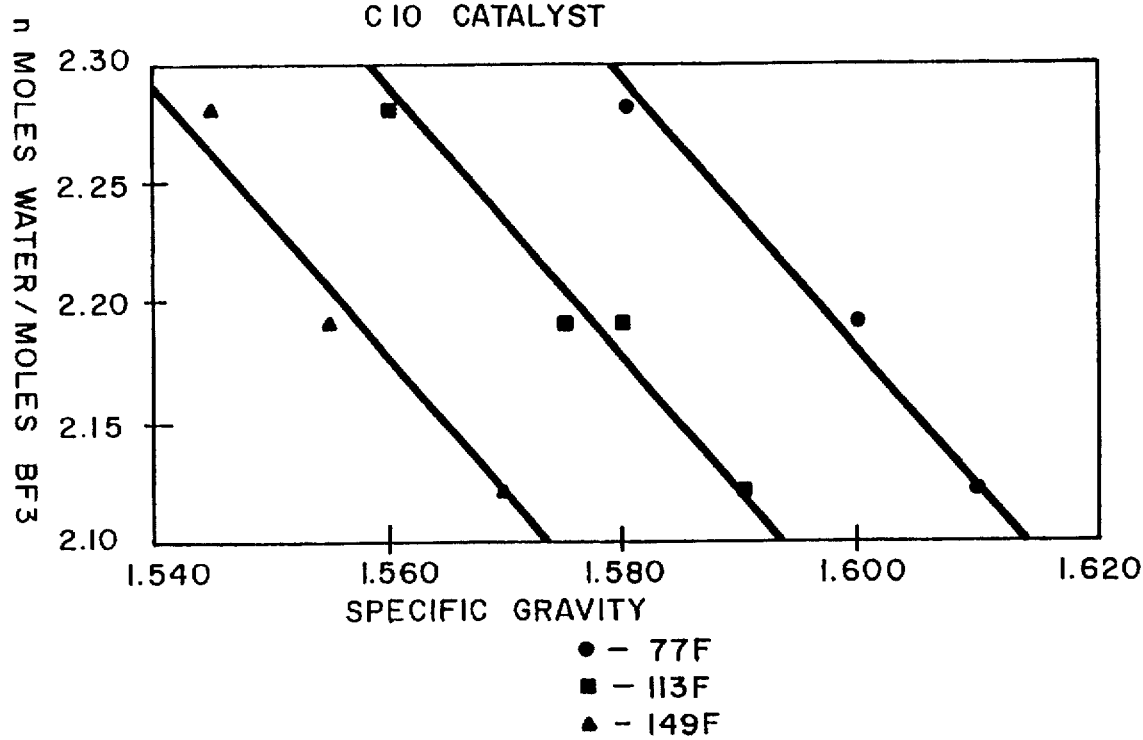
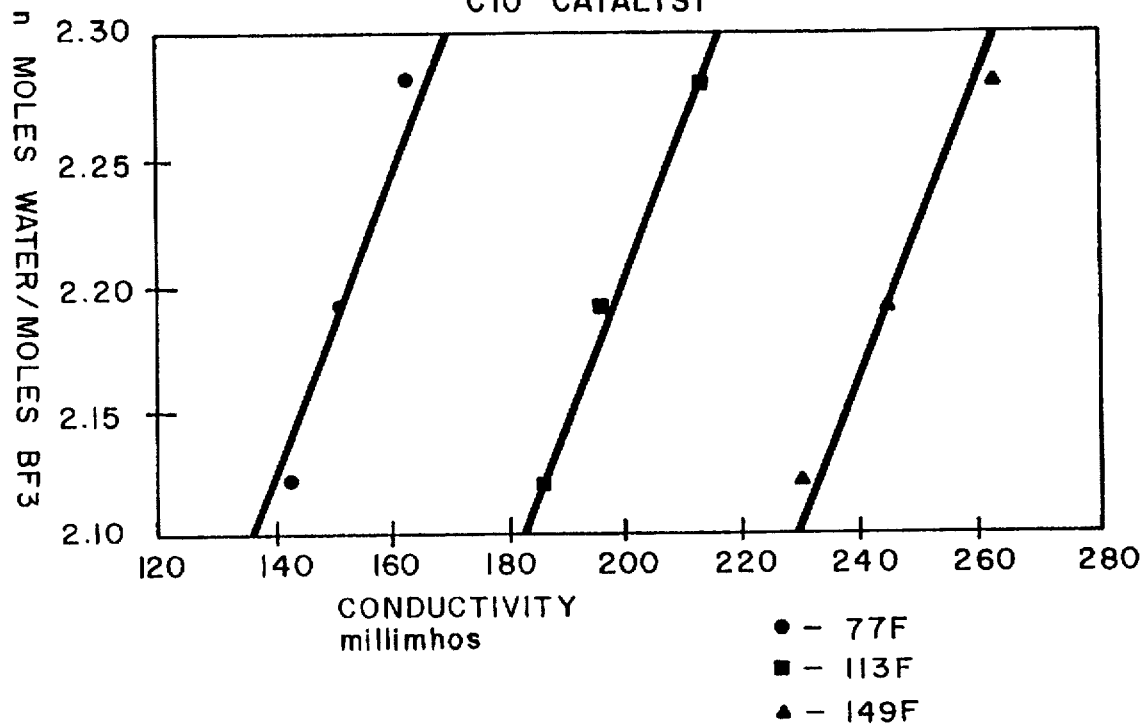

CONDUCTIVITY IS INDEPENDENT OF COMPLEX CONTENT C5 CATALYST

- ●-77F SAT'D W/COMPLEX
- □-113F
- △-149F
- ■-113F SAT'D W/COMPLEX
- ▲-149F SAT'D W/COMPLEX

CONDUCTIVITY OF BF3 CO CATALYST SYSTEMS BF3/H3PO4 (1/1) AT 25C

CATALYST REGENERATION PROCESS

BACKGROUND OF THE INVENTION

1. Field of the Invention

The present invention relates to a process for controlling the regeneration of boron trifluoride catalyst complexes in the production of carboxylic acids and other products made using boron trifluoride systems as a catalyst.

2. Description of Related Art

It is known in the art that mono-carboxylic acids may be prepared from olefin starting materials by the well known Koch synthesis by carbonylation of the olefin with carbon monoxide in the presence of strong acid catalysts to form the intermediate acyl ion complex, followed by hydrolysts to form the acid. A particularly facile process has been developed for the carbonylation of olefins utilizing boron trifluoride dihydrate as the acid catalyst. THUS, in a process described in "Hydrocarbon Processing", 44, 139 (1965), 2,2-dimethyl propionic-acid (also known as neo pentanoic acid) is prepared using a Koch synthesis by reacting isobutylene and carbon monoxide in the presence of $BF_3 \cdot 2H_2O$ followed by hydrolysis to produce the neo-acid. A similar process is described in French Patent 1252675 except that the catalyst used is a mixture of boron trifluoride or its hydrides and phosphoric acid. Other related processes are disclosed in U.S. Pat. Nos. 4,518,798, 3,349,107 and 3,527,779.

The overall chemical reaction producing neo-acids is as follows:

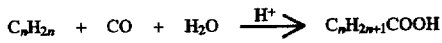

In this reaction, an acid with a carbon number one higher than the starting feed olefin is produced. Starting materials include isobutylene for neo-pentanoic ($C_5$) acid and branched nonenes for neo-decanoic ($C_{10}$) acid. Other acids can be produced by changing feedstock (for example, hexenes for $C_7$ acid or tetrapropylene for $C_{13}$ acid). The reaction sequence includes carbonylation of the olefin into an acid complex with an acid catalyst, and then hydrolysis to release the acid from the complex. Most of the preferred Koch processes use a boron trifluoride catalyst system containing water and sometimes a co-catalyst such as phosphoric acid or sulfuric acid. When such a co-catalyst is used, it is generally present at a molar ratio of from about 0.1 to about one mole per mole of boron trifluoride catalyst. The process requires the regeneration of the catalyst in a hydrolysis step in which the amount of hydrolysis water added is critical to the efficiency of the process.

A simplified flow diagram of the neo-acids process is shown in FIG. 1. Synthesis gas containing CO and hydrogen is concentrated by removing hydrogen via permeation, adsorption or cryogenic processes. The feed olefin, boron trifluoride dihydrate, and concentrated CO are then fed to a continuous well-mixed reactor where the olefin complexes at high pressure and low temperature. The reactor effluent is hydrolyzed to release crude acid and regenerate catalyst for recycle. The crude acid may subsequently ba treated and distilled to recover the finished acid products.

One of the major advantages associated with the use of $BF_3 \cdot 2H_2O$ as a catalyst in such processes is that it is very active in the reaction sequence for producing neo-acids and that it may be readily regenerated for recycle in the system from the complex formed between $BF_3 \cdot 2H_2O$ and the olefin and carbon monoxide reactants by careful control of the amount of water entering the hydrolysis unit. Control of the amount of water introduced determines whether the desired catalyst is regenerated with the optimum $H_2O$ to $BF_3$ ratio.

The common practice to determine catalyst strength and degree of hydration is by specific gravity measurement as an indication of the amount of water contained in the catalyst. These measurements may be taken where the catalyst exits the hydrolysis section am shown in FIG. 1. Based on the determination, the amount of water entering the hydrolysis section is adjusted as the case may be to maintain the specific gravity-within certain limits and thereby optimize the water content of the catalyst exiting the hydrolysis section and sent to recycle.

One of the problems associated with using specific gravity measurements is that the method cannot distinguish between a catalyst sample diluted with water or diluted with organic materials generated in the reaction process. Thus the method does not provide precise control in hydrolysis water adjustment due to this variable.

SUMMARY OF THE INVENTION

It was in view of the foregoing that the present invention has been conceived and is now reduced to practice. The invention, then, relates to a process for controlling the regeneration of boron dihydrate catalyst complexes in the production of carboxylic acids and other products using boron trifluoride as a catalyst. Catalyst strength is determined by measuring the electrical conductivity of the catalyst recovered from hydrolysis. If the conductivity is greater than a predetermined value, the hydrolysis water rate is reduced and if the conductivity is less than a predetermined value, the hydrolysis water rate is increased.

The invention enables the continuous monitoring of the strength of the catalyst as well as its continuous regulation to assure that recycled catalyst of a predetermined strength is made available at all times for reaction. A particularly desirable feature of the invention is the fact that conductivity is affected only by the water content of the complex containing the catalyst and is relatively unaffected by differences in organic content of the complex.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIG. 3 is an isotherm plot of $C_{10}$ catalyst water content as a function of specific gravity;

FIG. 4 is an isotherm plot of $C_{10}$ catalyst water content as a function of conductivity;

DESCRIPTION OF THE PREFERRED EMBODIMENT

A current practice used in the production of neo-carboxylic acids from olefins is the measurement of catalyst specific gravity as an indication of the amount of water contained in the catalyst. The water content is generally considered to be indicative of catalyst strength. Based on the gravities, hydrolysis water flow rate is adjusted to maintain catalyst gravity within specified limits.

However, it has been found that electrical conductivity is an attractive alternative to specific gravity for measuring catalyst water content and controlling hydrolysis water addition. The present invention results from this finding. There are a number of advantages for using conductivity instead of specific gravity. In a first instance, specific gravity cannot distinguish between dilution by water from dilution by organic compounds or complexes present in the catalyst mixture. These two situations require opposite responses in hydrolysis water adjustment. A catalyst which has a low specific gravity due to high water content requires a reduction in hydrolysis water rate. On the other hand, a catalyst with the same specific gravity but, instead due to high organic content, may already have too little water and thus requires an increase in hydrolysis water. Conductivity is very sensitive to the water content of catalyst and is relatively unaffected by differences in organic content. This characteristic makes it an especially attractive measurement for hydrolysis water adjustments.

The boron trifluoride hydrate-catalyst streams often exist as two liquid phases. This potentially two phase sample can cause an erroneous specific gravity measurement. Conductivity measurement, however, is not sensitive to this problem.

It is anticipated that the use of electrical conductivity to measure and control catalyst water content (catalyst strength) will affect a more stable operation at a level which is near optimum for the desired reaction.

Figure 1:
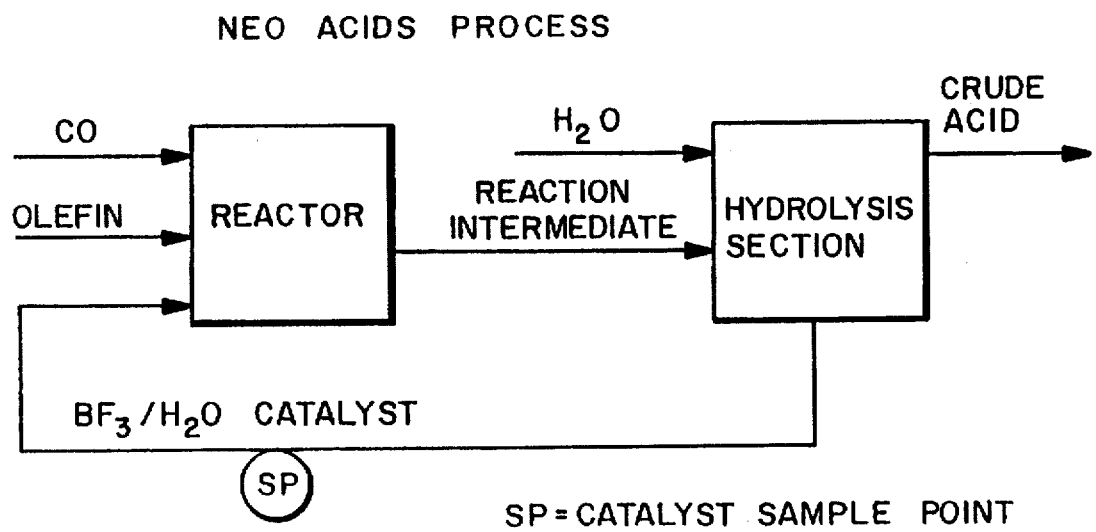
FIG. 1 is a flow diagram generally illustrating a process embodying the invention.

With reference to FIG. 1, the neo-acid manufacturing process was previously described. As illustrated, the feed olefin, boron trifluoride dihydrate and concentrated carbon monoxide are fed to a continuous well-mixed reactor where the olefin complexes at high pressure and low temperature. The olefin complex is then hydrolyzed to release crude acid and to regenerate the catalyst for recycle.

Figure 2:
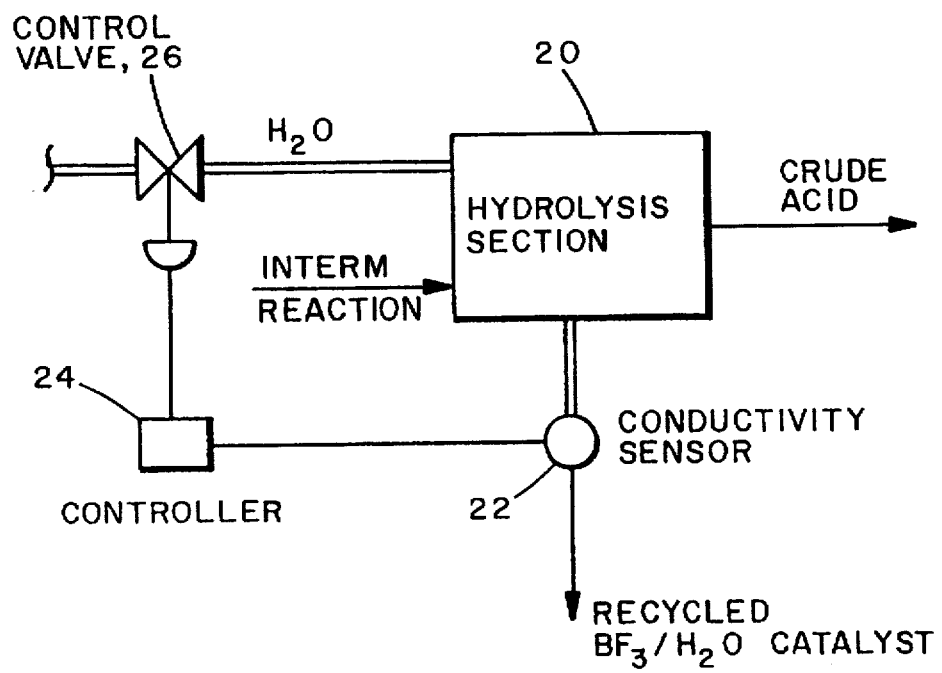
FIG. 2 a more detailed flow diagram illustrating specifics relating to the measurement of catalyst strength according to the invention.

With reference to FIG. 2, the process of the invention is most clearly shown. The strength of the regenerated catalyst issuing from the hydrolysis section 20 is determined with the aid of a conductivity sensor 22 which is in contact with the catalyst composition to be measured. A sensor suitable for purposes of the invention may be UNILOC Model 222 flow through torroidal conductivity sensor manufactured by Rosemont Analytical of Eden Prairie, Minn. The advantage of a toroidal sensor is that it is not in contact with the aggressive (corrosive) catalyst. Thereupon, a controller 24, responsive to operation of the sensor 22 is in turn operable to actuate a control valve 26. A controller suitable for purposes of the invention may be Model No. 222-01 manufactured by Rosemont Analytical, aforesaid.

It will be appreciated that if the conductivity as measured by the sensor 22 is below a predetermined value, the valve is to be opened further and if the conductivity is above a predetermined value, the valve is to be closed down.

The invention is further illustrated by the following examples, which, however, are not to be taken as limiting in any respect. Each experiment was designed with two independent variables and two dependent variables. The independent variables were temperature and catalyst water level. The dependent variables were specific gravity and conductivity. Temperature was controlled by immersing the samples in a constant temperature bath. Temperature range was chosen to span the conductivity standard temperature of 25° C. (77° F.) and a higher temperature of 150° F. A fairly narrow range of water level was chosen to ensure that the sensitivity of measurement is sufficient for adequate hydrolysis water control.

Water and boron levels were measured before and after an experimental run. These two measurements were used to calculate moles of water per moles of boron. Although a small amount of water was picked up by condensation from the water oath, it could easily be corrected using the post experiment analyses.

EXAMPLE 1

This example illustrates the use of boron trifluoride dihydrate catalyst for the production of neo-decanoic ($C_{10}$) acid.
Specific Gravity FIG. 3 is an isotherm plot of $C_{10}$ catalyst water content as a function of specific gravity. A good correlation was obtained.
Conductivity FIG. 4 is an isotherm plot of $C_{10}$ catalyst water content as function of conductivity. Measurement variability is virtually identical to specific gravity.

EXAMPLE 2

This example illustrates the use of boron trifluoride dihydrate catalyst for the production of neo-pentanoic ($C_5$) acid.
Specific Gravity There is a major difference between catalyst used in the $C_5$ and $C_{10}$ processes. $C_5$ catalyst contains a large amount of dissolved complex (and possibly free organic). When a $C_5$ catalyst sample cools, a separate phase of complex forms on the surface. In order to collect meaningful data, the catalyst used in these experiments was drained off the bottom of a separatory funnel to separate it from the upper complex layer. In this way, a homogeneous sample was obtained.

Figure 5:
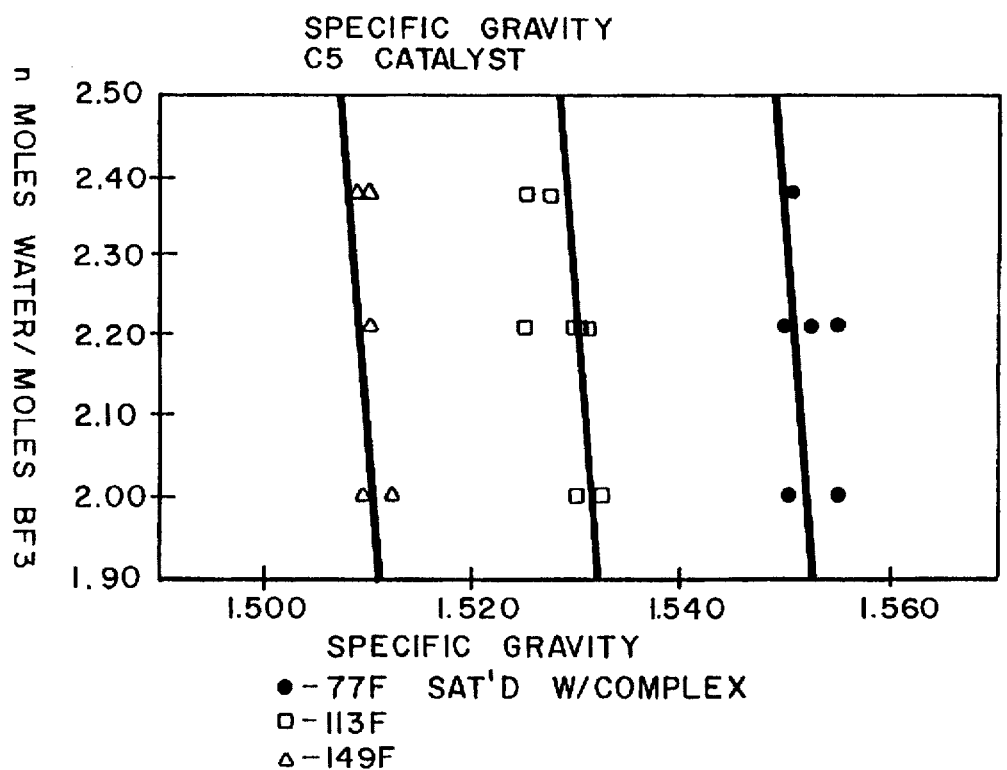
FIG. 5 is an isotherm plot of $C_5$ catalyst water content as a function of specific gravity;.

The above technique gave samples virtually saturated with complex at ambient temperature, but it must be noted that the heated samples in FIG. 5 (temperature >77° F.) are not saturated. Also, it must be noted that water which was added to prepare the medium and high water level catalyst samples hydrolyzed some neo-acid from the dissolved complex during sample preparation. The hydrolyzed acid was removed to obtain a homogeneous sample.

Complex saturation notwithstanding, a very insensitive relationship was observed between catalyst water content and specific gravity. The apparent cause of this phenomenon is that water addition which lowers gravity is partially offset by the specific gravity increase effect of the lost $C_5$ neo-acid which was hydrolyzed out of the catalyst. Hence, water addition had only a very subtle effect on specific gravity.
Effect of Complex Addition To measure the properties of catalyst saturated with complex at higher temperatures complex was added (2.2 wt. %) to the medium water level catalyst and the sample heated to 149° F. At this temperature, the complex dissolved and the saturation point was reached. That is, all but a barely visible amount of complex went into solution. Measurements were taken and the sample was cooled to 113° F. Partial phase separation was observed. Again, measurements were taken. The specific gravity reduction due to complex addition is shown in FIG. 6.

Figure 6:
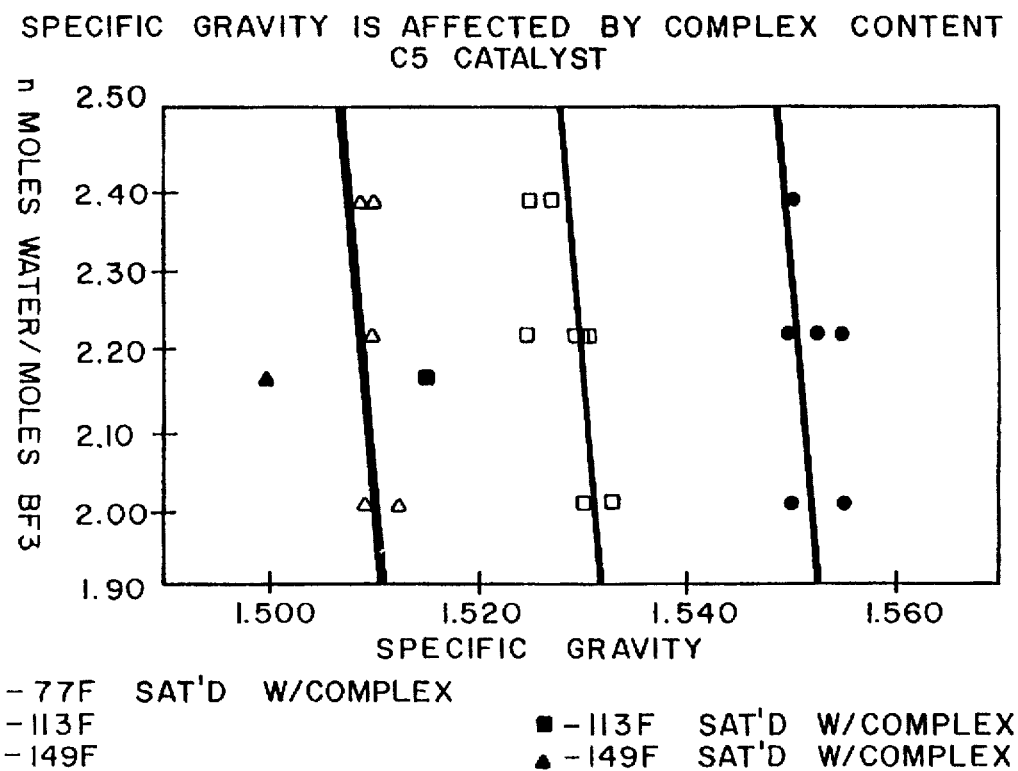
FIG. 6 is an isotherm plot of $C_5$ catalyst water content as a function of specific gravity wherein the catalyst has been saturated with complex.

As the data in FIG. 6 demonstrates, a large gravity deviation from the isotherm was observed when complex was dissolved in the catalyst. This shows the expected gravity lowering effect of complex dissolved in $C_5$ catalyst. Therefore, in order to determine the water level in a $C_5$ catalyst with specific gravity, another measurement is required which indicates the organic content.

Conductivity

Figure 7:
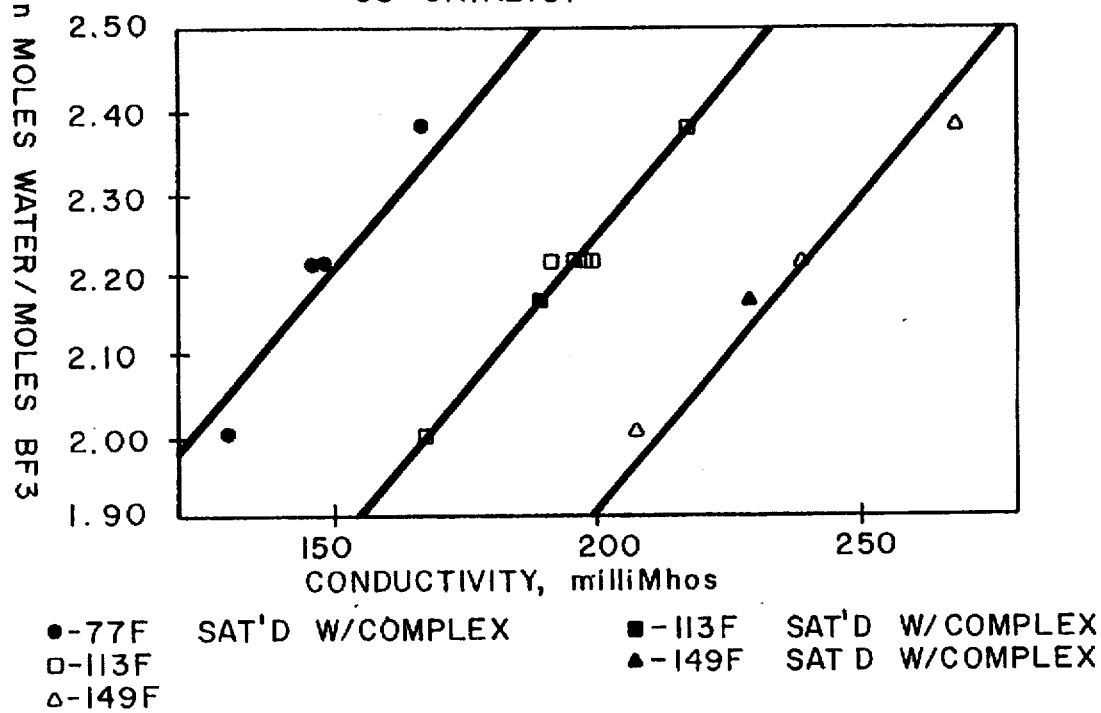
FIG. 7 is an isotherm plot of $C_5$ catalyst water content as a function of conductivity.

In contrast to specific gravity, FIG. 7 shows conductivity as a function of catalyst water content. Complex saturated catalyst measurements fall on the same isotherms as unsaturated measurements. Conductivity is apparently unaffected by dissolved complex. It is only a function of water content and temperature. This relationship makes conductivity an extremely useful tool for hydrolysis water control because it measures only the contained water without being affected by the organic content.

The data presented above indicates that electrical conductivity is a more effective way to measure catalyst water content than specific gravity. Unlike specific gravity, conductivity is a function only of the water content in a catalyst and not organic content which makes it a preferred analysis method.

EXAMPLE 3

Figure 8:
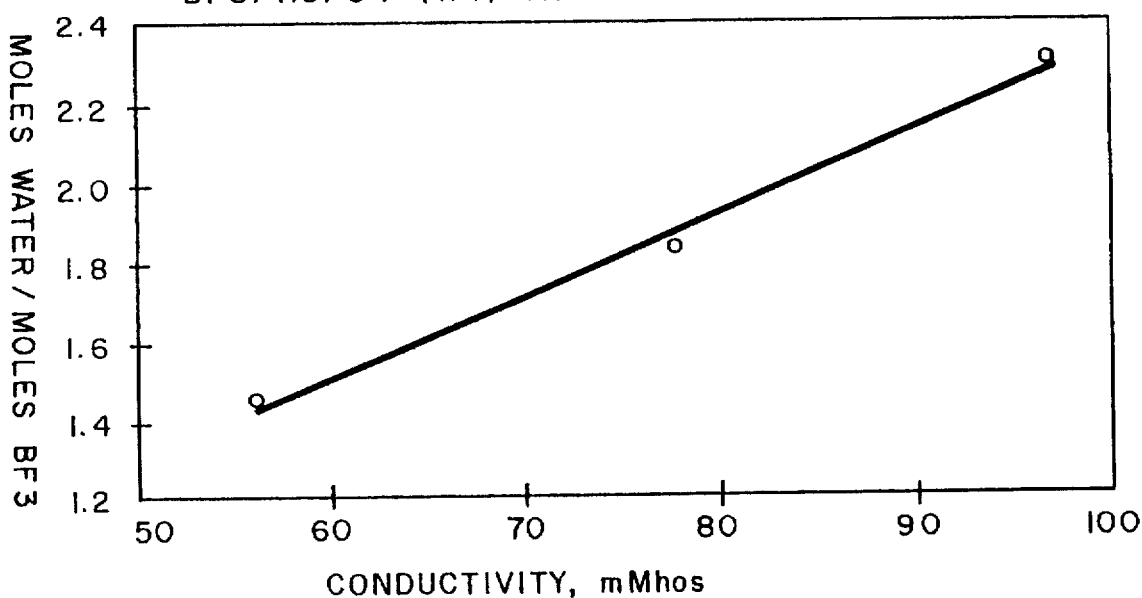
FIG. 8 is plot of the conductivity of $BF_3/H_3PO_4$ at 25° C.

This example illustrates the use of electrical conductivity to measure and control the water level in boron trifluoride catalysts containing the co-catalyst phosphoric acid. FIG. 8 shows data that indicates the strong relationship between electrical conductivity and water content. It follows that a similar relationship also exists for a $BF_3$ hydrate catalyst composition containing co-catalysts like sulfuric acid.

Conductivity instruments are commercially available as on-line analyzers which is an effective way to control hydrolysis water rate, as indicated in FIG. 2. Such a closed loop control scheme could maintain a consistent hydrolysis process which produces the optimum catalyst strength.

While preferred embodiments of the invention have been disclosed in detail, it should be understood by those skilled in the art that various other modifications may be made to the illustrated embodiments without departing from the scope of the invention as described in the specification and defined in the appended claims.

What is claimed:

1. In a continuous process for the production of aliphatic carboxylic acids by the reaction of an olefin and carbon monoxide in the presence of a catalyst comprising a $BF_3$ hydrate composition and the regeneration of said catalyst by control of the water content of said regenerated catalyst exiting hydrolysis, a method of determining catalyst strength as a function of the water content in the catalyst comprising the steps of:

(a) introducing water for hydrolysis of the reaction product of the olefin and carbon monoxide and for catalyst strength control;

(b) withdrawing the $BF_3$ hydrate composition catalyst resulting from hydrolysis;

(c) measuring the electrical conductivity of the catalyst complex exiting hydrolysis;

(d) continuously comparing the electrical conductivity measured in step with a predetermined value thereof;

(e) increasing the rate of introduction of water per step (a) in the event the electrical conductivity measured in step (c) is less than the predetermined value; and (f) decreasing the rate of introduction of water per step (a) in the event the electrical conductivity measured in step (c) is greater than the predetermined value.

2. A process as set forth in claim 1 wherein said $BF_3$ hydrate composition comprises $H_3PO_4$ as a co-Catalyst in a molar ratio with the $BF_3$ of up to one to one.

3. A process as set forth in claim 1 wherein said $BF_3$ hydrate composition comprises $H_2SO_4$ as a co-catalyst in a molar ratio with the $BF_3$ of up to one to one.

4. A process as set forth in claim 1 including the step of:

(g) reintroducing the $BF_3$ hydrate composition catalyst obtained in step (c) for reaction with the olefin and carbon monoxide.

5. A process as set forth in claim 1 wherein step (b) is performed by a toroidal conductivity sensor.

6. A process for the introduction of aliphatic carboxylic acid comprising the steps of:

(i) reacting an olefin and carbon monoxide in the presence of a catalyst comprising a $BF_3$ hydrate composition;

(j) introducing water to thereby perform hydrolysis of the reaction product resulting from step (i);

(k) recycling the $BF_3$ hydrate composition catalyst resulting from step (j), reintroducing it for reaction with the olefin and carbon monoxide;

(l) measuring the electrical conductivity of the hydrate composition catalyst following step (j);

(m) continuously comparing the electrical conductivity measured in step with predetermined value thereof;

(n) increasing the introduction of water per step (j) in the event the electrical conductivity measured in step (l) is less than the predetermined value; and (o) decreasing the introduction of water per step (j) in the event the electrical conductivity measured in step (l) is greater than the predetermined value.

* * * * *